United States Patent [19]

Kelman

[11] Patent Number: 4,871,363
[45] Date of Patent: Oct. 3, 1989

[54] CORRECTIVE INTRAOCULAR LENS

[76] Inventor: Charles D. Kelman, 721 Fifth Ave., New York, N.Y. 10022

[21] Appl. No.: 222,133

[22] Filed: Jul. 21, 1988

[51] Int. Cl.⁴ .............................................. A61F 2/16
[52] U.S. Cl. ......................................................... 623/6
[58] Field of Search ............................................. 623/6

[56] References Cited

U.S. PATENT DOCUMENTS

| 2,834,023 | 5/1958 | Lieb | 623/6 |
|---|---|---|---|
| 4,174,543 | 11/1979 | Kelman | 623/6 |
| 4,253,200 | 3/1981 | Kelman | 623/6 |
| 4,296,501 | 10/1981 | Kelman | 623/6 |
| 4,370,760 | 2/1983 | Kelman | 623/6 |
| 4,403,353 | 9/1983 | Tennant | 623/6 |
| 4,442,553 | 4/1984 | Hessburg | 623/6 |

OTHER PUBLICATIONS

"Lens Styles from Cilco", Brochure of Cilco, Inc. (6 Pages), pp. 1, 2 & 6 Cited, Styles MT-3-MT-7 and ST-1-ST-5 Shown on Page 2 Relied Upon, Oct. 1982, 623-6.

Primary Examiner—Ronald L. Frinks
Attorney, Agent, or Firm—Henry Sternberg; Bert J. Lewen

[57] ABSTRACT

Corrective intraocular lens for use with an intact natural eye lens, by insertion through an incision into the eye and implantation therein in spaced relation to the natural lens, including a lens body having a pair of opposed haptics constituting a first insertable leading haptic and a last insertable trailing haptic, each outwardly terminating in a transverse edge having a pair of laterally spaced apart and outwardly projecting contact lobes for engaging an adjacent eye tissue portion at a corresponding pair of spaced apart tissue points, the trailing haptic transverse edge having a 2-3 mm length, and the leading haptic transverse edge having a length larger than 2-3 mm and preferably about as large as the lens body diameter, such that the 2-3 mm length transverse edge of the last inserted haptic may be passed inwardly of the incision under minimum deflection of the intraocular lens and minimum risk of contact with the natural lens by the intraocular lens during implantation.

11 Claims, 2 Drawing Sheets

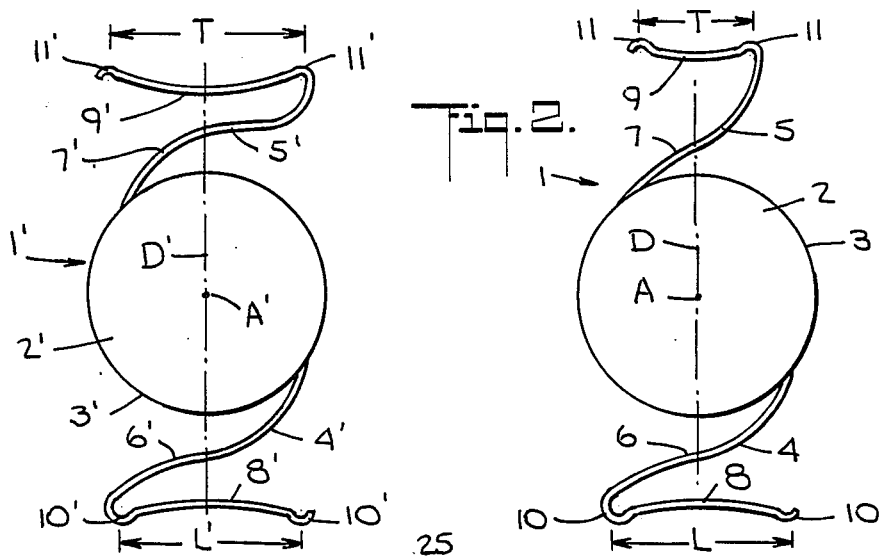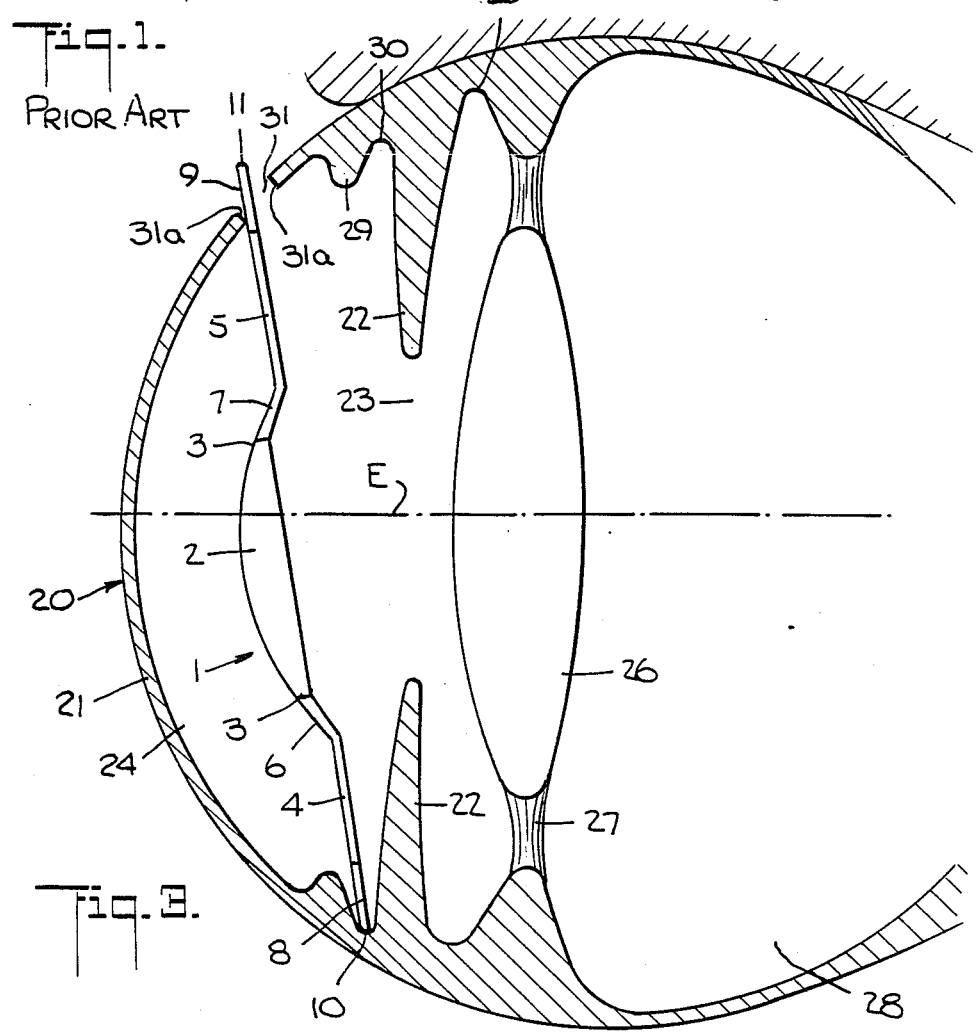

CORRECTIVE INTRAOCULAR LENS

FIELD AND BACKGROUND OF THE INVENTION

The present invention relates to a corrective intraocular lens, and more particularly to an artificial intraocular lens for use as an anterior chamber lens with an intact natural eye lens for correcting high myopia thereof, by insertion through an incision into the eye and implantation in the anterior chamber in spaced relation to the natural lens, in which the lens body or optic is provided with a pair of position fixation haptics which are differentially sized to aid safe insertion of the intraocular lens without damage to the natural lens during implantation.

For treatment of conditions such as high myopia of the natural eye lens, a known surgical procedure is to insert a corrective intraocular lens through an incision in the cornea of the eyeball, and implant such lens in the anterior chamber of the eye in spaced relation to the intact natural eye lens.

In these cases, since the natural lens remains intact, any foreign body introduced into the eye, such as an intraocular lens, must be introduced with the greatest of care by the surgical procedure used, so as to avoid any contact with the natural lens. This is because any contact with the sensitive natural lens by the foreign body could readily result in the natural lens becoming cataracted and/or in other injury to the natural lens of a serious, permanent nature.

Such injury is most likely to occur when maneuvering the intraocular lens during its insertion and seating in the eye, given the adverse conditions inherently involved, such as the confined space within the eye anteriorly of the intact natural lens, the fluid environment within the eye, the desire to keep the size of the corneal incision as small as possible to minimize trauma to the patient, the physical shape, size and make-up of the intraocular lens itself, and especially of its outwardly extending position fixation means, e.g. haptics, and the like.

In regard to the implantation of an anterior chamber intraocular lens for correcting the condition of a patient suffering from high myopia, for instance, the typical lens body or optic of the known type intraocular lens has a diameter of about 6 mm, and is provided with a pair of generally diametrically opposed and resiliently deflectable haptics of common shape and size, each terminating in a transverse edge portion having a typical length of about 6 mm and provided at its ends with a pair of similarly laterally spaced apart and outwardly projecting contact lobes for engaging the adjacent eye tissue in the anterior chamber, especially in the angle groove or "angle" defined between the scleral spur and the iris, by way of four point fixation technique.

These lobes may generally have a radius of about 0.125–0.25 mm, such that the outwardly projecting crests of the lobes are located about 0.125–0.25 mm beyond the remainder of the given transverse edge portion, and a like distance inwardly from the end edges of the transverse edge portion, making the length between the crests correspondingly about 5.75–5.5 mm for the typical 6 mm length transverse edge portion-containing haptic, these crests forming spaced-contact points engageable with the eye tissue.

As implanted, the intraocular lens is normally anteriorly of the iris and posteriorly of the scleral spur, but in any case is in spaced relation to the intact natural lens. It will be appreciated that, since the distance along the optical axis of the eye from the posterior surface of the cornea to the anterior surface of the natural lens is only about 3 mm, the intraocular lens must be inserted and implanted in the anterior chamber while maintaining it precisely parallel to the natural lens, so as to avoid twisting of the intraocular lens, which may cause it to touch the closely adjacent natural lens and result in serious, permanent damage thereto.

To accommodate such precise positioning of the intraocular lens, inasmuch as the angle groove normally has a diameter of about 12.5 mm, the overall longitudinal dimension of the known type intraocular lens from the transverse edge portion contact lobes of one haptic to those of the other haptic is usually about 13 mm.

The typical corneal incision is of a length just sufficient to accommodate the breadth of the optic during insertion, and in the normal case of an optic of about 6 mm diameter the incision length will likewise be about 6 mm. The location of the incision is usually somewhat anteriorly of the scleral spur and slightly closer to the optical axis of the eye than the scleral spur in terms of the spherical eyeball shape.

This means that, because of the anterior position of the incision relative to the angle groove, the linear distance between the line joining the end points of the incision and the most distant portion of the angle groove will be less than the above noted overall longitudinal dimension of about 13 mm from the transverse edge portion contact lobes of one haptic to the transverse edge portion contact lobes of the other haptic of the known type intraocular lens, such linear distance typically being only about 11 mm.

Hence, upon insertion in the usual case of the first or leading haptic through the incision, followed by the optic, and positioning of the leading haptic transverse edge portion contact lobes in seating engagement with the adjacent eye tissue portion in the angle groove most distant from the incision, the second or trailing haptic will remain outside of the eyeball, projecting outwardly from the incision a distance of about 1–2 mm.

To complete the insertion of the known type intraocular lens, substantial distortion thereof is necessary to squeeze all parts of the second or trailing haptic through the incision. Not only does the relatively unstable force transmission during this squeezing action potentially cause trauma to the eye tissue being placed under tensioning pressure, but it also raises the risk, as noted above, that the optic is caused to twist and as a result could touch the natural lens and cause permanent and serious injury thereto.

Considering the small size of the eyeball, and particularly of its interior portions as pertinent to the positioning of the known type intraocular lens, it becomes extremely important to maintain such lens out of contact with the natural lens, i.e. free from possible rotation and/or other substantial anterior or posterior displacement during insertion and seating of the intraocular lens.

It will be realized that the haptic transverse edge portions have a standard length dimension of relatively pronounced size, typically about 6 mm, so that the contact lobes thereon will be laterally spaced apart approximately a like distance, sufficient to provide stable positioning of the known type intraocular lens in the eye, especially at diametrically opposed portions of the angle groove. As a consequence, during final squeezing of the intraocular lens to force the still exposed trailing haptic inwardly of the corneal incision, the transverse edge portion thereof, especially where formed as a limb extending from a base stem situated on the optic peripheral edge, must be carefully negotiated through the incision in awkward, yet delicate, manner.

In this regard, the trailing haptic transverse length is as long as the incision when the "lips" of the incision are closed, yet it still extends outwardly of the eyeball and requires a spreading of the lips of the incision for insertion thereof. Such spreading, however, results in a shortening of the incision, thereby making the task of insertion even more difficult. Hence, while the leading haptic can be readily "snaked" through the incision, such "snaking" is not possible for the trailing haptic.

Since the typical length of the haptic transverse edge portions is about 6 mm and that of the incision is about 6 mm, when squeezing the known intraocular lens to force the last part of the trailing haptic inwardly of the incision, little tolerance exists between the incision and trailing haptic transverse edge portion, and this intensifies the danger of accidental twisting of the optic and possible injury to the closely disposed natural lens.

U.S. Pat. No. 4,174,543, issued Nov. 20, 1979, to Kelman discloses an intraocular lens having a small size optic, and a pair of generally diametrically opposed deflectable position fixation haptics extending outwardly therefrom, each provided with an outer transverse edge portion having a pair of laterally spaced apart contact lobes or the like for four point fixation in the eyeball, e.g. at generally diametrically opposed pairs of tissue points in the angle groove, upon insertion of the intraocular lens through a corneal incision.

Although the known type intraocular lens of this patent can be implanted as a corrective lens for use with an intact natural lens, it is primarily taught as a replacement for the natural lens upon extracapsular removal of the latter, e.g. to correct a condition such as aphakia, after removal of a cataracted natural lens. In the case where the natural lens is surgically removed, there is no danger of injury thereto when the intraocular lens is inserted through the incision into the eye.

Hence, in use of the intraocular lens of this patent as a replacement for the removed natural lens, the length of the common size and shape leading and trailing haptic transverse edge portions which contain the laterally spaced apart pairs of contact lobes or the like is not critical. In practice, as earlier noted, this length is about 6 mm to afford relatively maximum stability of lens fixation by providing correspondingly thereon similarly spaced apart contact lobes, while the overall longitudinal length from one such pair of contact lobes to the opposing pair, i.e. in undeformed or relaxed condition, is about 13 mm for accommodation in the approximately 12.5 mm diameter angle groove of the eye.

In such case, although the intraocular lens of this patent is squeezed in order to insert the exposed trailing haptic, the only risk is that accidental dislodgment of the already positioned leading haptic will require readjustment and repeating of the manipulation, with at most temporary trauma to any adjacent tissue that might be touched, but without any danger of injury to the natural lens, as the latter has already been removed per the contemplated procedure. On the other hand, where the intraocular lens of this patent is implanted as a corrective lens for an intact natural lens, the above noted problems and dangers regarding the natural lens are directly encountered.

U.S. Pat. No. 4,253,200, issued Mar. 3, 1981 to Kelman shows an intraocular lens having an optic provided with a pair of diametrically opposed haptics, one of which is longer than the other in radial distance as measured between the optical axis of the optic and the outer end of the haptic. These haptics do not contain spaced apart pairs of opposing contact lobes for four point fixation. Instead, the intraocular lens is used as a replacement for a natural eye lens, upon extracapsular removal of the latter, such that the radially longer haptic is positioned in linear contact with the ciliary sulcus and the radially shorter haptic is positioned in linear contact with the capsular bag from which the natural lens has been removed.

It would be desirable to provide a corrective intraocular lens for implantation in an eye, for use with an intact natural eye lens, permitting efficient insertion of the intraocular lens through a minimum size corneal incision, e.g. of length corresponding substantially to the diameter of the optic of the intraocular lens, especially in the case of an anterior chamber for correcting high myopia eyes, with minimum danger to the patient from accidental touching of the natural lens during the insertion procedure, and at the same time provide for adequate stability of fixation of the intraocular lens once implanted.

SUMMARY OF THE INVENTION

It is among the objects of this invention to provide a corrective intraocular lens for use with an intact natural eye lens, by insertion through a minimum size incision into an eye and implantation therein in spaced relation to the natural lens, including a lens body or optic having leading and trailing position fixation means permitting adequate stability of fixation of the intraocular lens once implanted, and which during insertion and implantation exposes the patient to minimum risk of contact with the natural lens by the intraocular lens.

According to one aspect of this invention, a corrective intraocular lens is provided for use as an anterior chamber lens with an intact natural eye lens for correcting high myopia thereof, by insertion through an incision into the eye and implantation in the anterior chamber in spaced relation to the natural lens. The corrective intraocular lens comprises a lens body or optic, and a pair of generally diametrically opposed resiliently deflectable position fixation haptics extending outwardly from the lens body and arranged for positioning the intraocular lens in the eye in spaced relation to the natural lens.

The haptics constitute a leading haptic and a trailing haptic, each comprising a pliable strand having a stem portion attached to the lens body and a limb portion extending from the stem portion and terminating in the transverse edge portion disposed crosswise of a longitudinal diametric line passing through the lens body and intersecting both transverse edge portions. Each transverse edge portion has a pair of laterally spaced apart and outwardly projecting contact lobes at the corresponding transverse ends thereof for engaging an adjacent eye tissue portion at a corresponding pair of spaced apart tissue points, whereby to form two generally diametrically opposed pairs of laterally spaced apart fixation points for positioning the intraocular lens in the eye.

Significantly, the trailing haptic transverse edge portion has a short length of about 2-3 mm, the lens body has a diameter of at least about two times the length of the trailing haptic transverse edge portion, and the leading haptic transverse edge portion has a longer length substantially larger than about 2-3 mm and preferably the same size as the lens body diameter.

In this way, for implantation the intraocular lens may be inserted into the eye through the incision of length corresponding substantially to the lens body diameter, by first snaking the leading haptic through the incision, next passing the lens body through the incision and positioning the leading haptic contact lobes in engagement with an eye tissue portion distal from in incision, and then passing the trailing haptic through the incision.

During the passing of the trailing haptic through the incision, the lips of the incision are maintained slightly spaced apart to form an enlarged gap between the lips in which the widest part of the gap is located centrally of the incision, and moving the trailing haptic through the widest part of the gap, while exerting minimum pressure on the intraocular lens in a direction towards the previously positioned leading haptic contact lobes just sufficient to deflect the trailing haptic transverse edge portion to clear the gap and approach and engage its contact lobes with a corresponding eye tissue portion proximate to the incision, for positioning the intraocular lens in spaced relation to the natural lens.

Such procedures are effectively able to be carried out under minimum deflection of the intraocular lens and minimum risk of contact with the natural lens by the intraocular lens during the implantation.

Conveniently, each haptic may be formed as a generally sinusoidal continuous strand having its stem portion attached to the lens body in the vicinity of the lens body periphery.

According to a favorable feature, the dimension of the trailing haptic in generally radial direction between the optical axis of the lens body and the trailing haptic contact lobes is slightly larger than the corresponding dimension of the leading haptic in generally radial direction between such lens body optical axis and the leading haptic contact lobes, sufficient to compensate for the larger length of the leading haptic transverse edge portion relative to the trailing haptic transverse edge portion length, for more precise positioning of the intraocular lens with the contact lobes of the haptics in engagement with the respective adjacent eye tissue portions.

According to another aspect of this invention, a method of implanting the corrective intraocular lens is provided, comprising carrying out the foregoing insertion and manipulation steps.

BRIEF DESCRIPTION OF THE DRAWINGS

Other objects of the invention will become apparent from the within specification and accompanying drawings, in which:

FIG. 1 is a schematic view of the front or anterior side of a PRIOR ART intraocular lens, having a pair of diametrically opposed haptics outwardly terminating respectively in leading and trailing transverse edge portions of the same length, each having a pair of equally laterally spaced apart and outwardly projecting contact lobes, shown for purposes of comparison with the intraocular lens improvement according the invention;

FIG. 2 is a schematic view similar to FIG. 1, showing an embodiment of a corrective intraocular lens according to the invention, wherein the trailing haptic transverse edge portion is of smaller length than that of the leading haptic transverse edge portion;

FIG. 3 is a schematic exaggerated sectional view of an eye showing the manner of inserting the corrective lens of FIG. 2 through a corneal incision thereinto for implantation in spaced relation to the intact natural eye lens;

DESCRIPTION OF THE PREFERRED EMBODIMENTS

Figure 4:
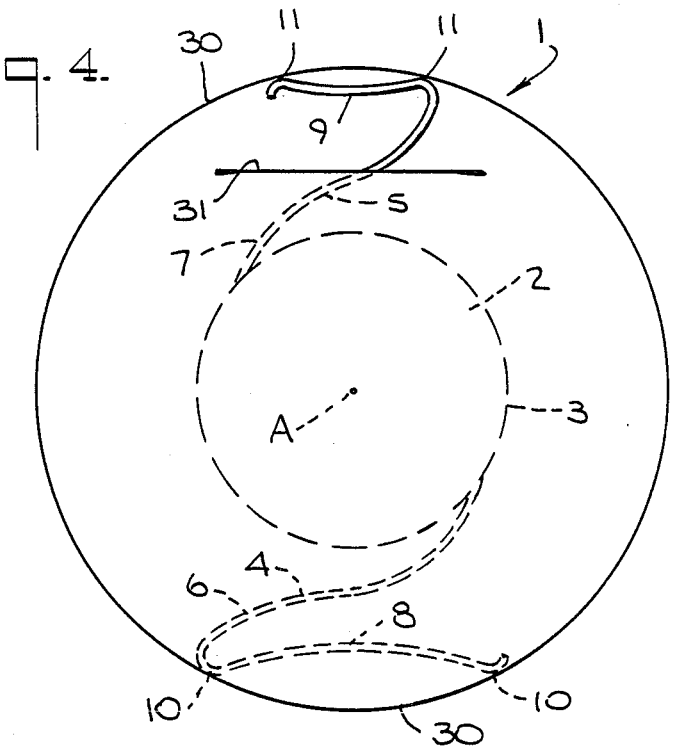
FIG. 4 is a schematic exaggerated front projection view of the arrangement of FIG. 3, showing the intraocular lens partly inserted through the incision into the eye.

Referring to the drawings and initially to FIG. 1, a PRIOR ART intraocular lens 1' is shown, for example of the type contemplated in said U.S. Pat. No. 4,174,543 to Kelman, formed of a lens body or optic 2' having a peripheral edge 3', and a pair of generally diametrically opposed position fixation haptics, denoted leading haptic 4' and trailing haptic 5', of common size and shape, attached to optic 2', preferably integrally, in the vicinity of peripheral edge 3' and arranged for positioning lens 1' in the eye.

Haptics 4' and 5' are typically of generally sinusoidal continuous strand conformation, and are resiliently deflectable, e.g. formed as pliable strands. Haptics 4' and 5' are respectively composed of the leading stem 6' and trailing stem 7', attached at opposed locations to optic 2', and which extend generally radially outwardly from peripheral edge 3', and terminate in the generally transverse leading limb 8' and trailing limb 9' correspondingly extending from the stems 6' and 7'.

Limbs 8' and 9' may be slightly radially inwardly bowed toward the optical axis A' of optic 2', but in any case constitute transverse edge portions respectively containing at their transverse or crosswise ends the laterally spaced apart pairs of generally radially outwardly projecting leading contact lobes 10', 10' and trailing contact lobes 11',11' for engaging adjacent portions of the eye tissue when inserted for implantation. Leading lobes 10',10' and trailing lobes 11',11' serve to space the corresponding crosswise intermediate spans of limbs of transverse edge portions 8' and 9' from the adjacent eye tissue, whether such spans are bowed or not.

In effect, each of haptics 4' and 5' extends outwardly from peripheral edge 3' and terminates in a respective transverse edge portion 8' or 9' which is disposed crosswise of a longitudinal diametric line passing through optic 2', e.g. at axis A', and intersecting both such edge portions 8' and 9'. Thus, the pairs of leading lobes 10',10' and trailing lobes 11',11' at the respective crosswise ends of transverse edge portions 8' and 9' are positioned for engaging generally diametrically opposed adjacent eye tissue portions at corresponding respective pairs of spaced apart tissue points, whereby to form two generally diametrically opposed pairs of laterally spaced apart fixation points for positioning lens 1' in the eye.

This known type intraocular lens arrangement is typically regarded as a "Quadraflex" lens arrangement, which permits relatively stable four point fixation of the lens system in the eye, the generally diametrically opposed pairs of fixation points being equally laterally spaced apart in dependence upon the equal lateral spacing of the pairs of contact lobes 10',10' and 11',11', as the case may be.

In the case of using lens 1' as a corrective intraocular lens with an intact natural lens, typically optic 2' has a diameter of about 6 mm, limbs 8' and 9' commonly have a transverse length of about 6 mm, thereby typically providing a 5.75 or 5.5 mm lateral distance L' between leading lobes 10',10' (center to center), i.e. between the outwardly projecting crests thereof, depending on whether such lobes have a radius of 0.125 or 0.25 mm, and a like 5.75 or 5.5 mm (center to center) lateral distance T' between trailing lobes 11',11', and an overall longitudinal dimension D' in generally diametric direction between the opposed pairs of leading lobes 10',10' and trailing lobes 11',11' of about 13 mm.

For implantation, e.g. in case of a corrective intraocular lens for use with an intact natural lens to correct high myopia, this known type intraocular lens 1' is typically inserted through a corneal incision of size or length sufficient for optic 2' to pass inwardly therethrough, by first passing leading haptic 4' through the incision, e.g. by "snaking" limb 8' and then stem 6' between the sides or lips of the incision, next passing optic 2' through the incision, e.g. by slipping this disclike part through the surrounding incision girth, and seating leading lobes 10',10' against the adjacent tissue in the eye, e.g. in the angle groove located posteriorly of the scleral spur and anteriorly of the iris, and finally squeezing the still exposed trailing haptic 5' through the incision.

For the last step to be accomplished, the transverse length T' of trailing limb 9' must be pushed through the incision under the now cocked or preloaded force of the squeezing action, while the opposing leading haptic 4' is stationarily engaged via its lobes 10',10' with the eye tissue, thereby forming a thrust pivot force transmission system in which leading lobes 10',10' serve as a composite thrust pivot. This inherently causes an unstable condition to occur, rendering the distal trailing limb 9' prone to wobbling back and forth, relative to the proximate leading limb 8' as pivot center, as trailing limb 9' is being inserted between the lips of the incision under compression.

Consequently, the manipulation of the trailing limb 9' inwardly of the incision is difficult to carry out, and exposes the procedure to mishap, such as twisting and tilting of the optic toward the natural lens of the eye. Such is aggravated by the comparatively large length of trailing limb 9' relative to the incision length, these typically being of about the same dimensions, i.e. 6 mm.

Hence, under the cocked or preloaded forces involved, such dimensions detract from the efficiency of the operation, already fraught with adverse conditions such as the confined space and fluid environment within the eyeball, and the small size of the corneal incision, aside from the shape, size and make-up of the intraocular lens. This procedure is to be distinguished from the case of extracapsular removal of the natural lens and its replacement by the intraocular lens, since the danger is not as great, inasmuch as the natural lens has already been removed and one need not be concerned about its safety.

Thus, where the intraocular lens insertion is carried out while an intact natural eye lens remains in place, the above described procedure must be most carefully effected to avoid all potential sources of trauma and possible damage to the natural lens, as it is only being supplemented by the internal implant lens and not replaced thereby.

By way of this invention, an improved construction and cognate implantation method are provided for such purposes.

In essence, as shown in FIGS. 2–5, an intraocular lens 1 according to an embodiment of the invention, is constructed as a corrective artificial lens for use with the intact natural eye lens, and has like parts to those of the known type lens 1' shown in FIG. 1, and for the same purpose, except mainly for the shorter length dimension or size of the trailing limb and the distance between its contact lobes.

Specifically, as shown in FIG. 2, corrective intraocular lens 1 has a lens body or optic 2 of a selective diameter, e.g. of about 6 mm, provided with a peripheral edge 3 to which a pair of generally diametrically opposed position fixation haptics, denoted leading haptic 4 and trailing haptic 5, are attached. Haptics 4 and 5 comprise resiliently deflectable means such as, e.g. generally sinusoidal continuous, pliable strands, respectively having generally radially outwardly extending leading and trailing stems 6 and 7 attached to optic 2 in the vicinity of peripheral edge 3, and transverse leading and trailing limbs 8 and 9 extending outwardly from stems 6 and 7 and forming transverse edge portions.

However, while the transverse length L of leading limb 8 is of typical standard large size, e.g. about 6 mm, the transverse length T of trailing limb 9 is much shorter, and is specifically about 2–3 mm in length. In turn, the laterally spaced apart and outwardly projecting leading contact lobes 10,10 are of like spacing relative to the length of leading limb 8, e.g. also 5.75 or 5.5 mm apart, center to center, i.e. between the lobe crests, depending on whether such lobes have a radius of 0.125 or 0.25 mm, whereas the laterally spaced apart and outwardly projecting trailing contact lobes 11,11 are of short spacing relative to the length of trailing limb 9, i.e. also about 2–3 mm apart.

More particularly, where lobes 11,11 have a radius of about 0.125–0.25 mm, their outwardly projecting crests are located about 0.125–0.25 mm beyond the remainder of their transverse edge portion 9, and a like distance inwardly from the end edges of such transverse edge portion, such that while the length between the laterally opposed end edges of transverse edge portion 9 will be about 2–3 mm, the corresponding length between the crests will actually be about 1–2.5 mm in dependence upon said lobe radius.

Leading and trailing limbs or transverse edge portions 8 and 9 are thus disposed crosswise of the longitudinal diametric line passing through optic 2, e.g. at optical axis A, and intersecting both transverse edge portions 8 and 9, with the longitudinal dimension D in generally diametric direction between the opposed pairs of leading lobes 10,10 and trailing lobes 11,11 being typically about 13 mm.

Lens 1 is favorably provided as a anterior chamber lens for implantation in the anterior chamber of the eye for correcting high myopia eyes. Since lens 1 must be maintained in spaced relation to the intact natural eye lens, and desirably also in spaced relation to the iris to permit unhindered normal adjustment movement thereof, haptics 4 and 5, and particularly stems 6 and 7, are favorably offset axially relative to the main plane of optic 2 in a direction posteriorly, so as to space optic 2 safely anteriorly from the natural lens and from the iris, although arranged generally coaxially with the natural lens to provide the desired corrective optical system in the eye (cf. FIG. 3).

As shown in FIGS. 3, the eyeball 20 includes the cornea 21, the iris 22 which forms the adjustable central pupil opening 23 and which separates the anterior chamber 24 from the posterior chamber 25, and the intact natural eye lens 26, located by the zonules or suspensory ligament and fibers 27, attached to its periphery, in posterior chamber 25. Anterior chamber 24 is provided with the circumferential scleral spur 29 anteriorly of iris 22, between which is defined the circumferential angle groove or "angle" 30 which typically has a diameter of about 12.5 mm.

As also shown in FIG. 3, in carrying out the implantation procedure according to this invention, a corneal incision 31 is typically made of a length corresponding to the diameter of optic 2, e.g. about 6 mm, and in crosswise direction at a spherical level relative to eyeball 20 slightly anteriorly spaced from scleral spur 29 and thus slightly closer than scleral spur 29 to the optical axis E of the eye. This means that the distance from incision 31 to the farthest point in angle groove 30 will be less than 13 mm, and is typically only 11 mm, due to the anteriorly offset location of incision 31 relative to the plane passing through angle groove 30.

Lens 1 is inserted through incision 31 by first passing leading haptic 4 between the incision edges or lips 31a, 31a, e.g. by "snaking" leading limb 8 and stem 6 therethrough, next passing optic 2 through the surrounding girth of incision 31, and then negotiating the already inserted leading haptic 4 so that leading limb 8 enters the most distant portion of angle groove 30 and in turn its pair of leading lobes 10,10 is placed in aligned engagement with a corresponding pair of spaced tissue points within angle groove 30.

At this stage, as shown in FIGS. 3-4, trailing haptic portion 9 remains exteriorly of incision 31, and extends a distance of about 2 mm outwardly thereof.

It will be realized that since incision 31 is desirably kept as short in length as possible so as to minimize trauma to the patient, its length is normally just sufficient for the diameter of optic 2 to clear incision lips 31a, 31a and slide inwardly of incision 31.

Figure 5:
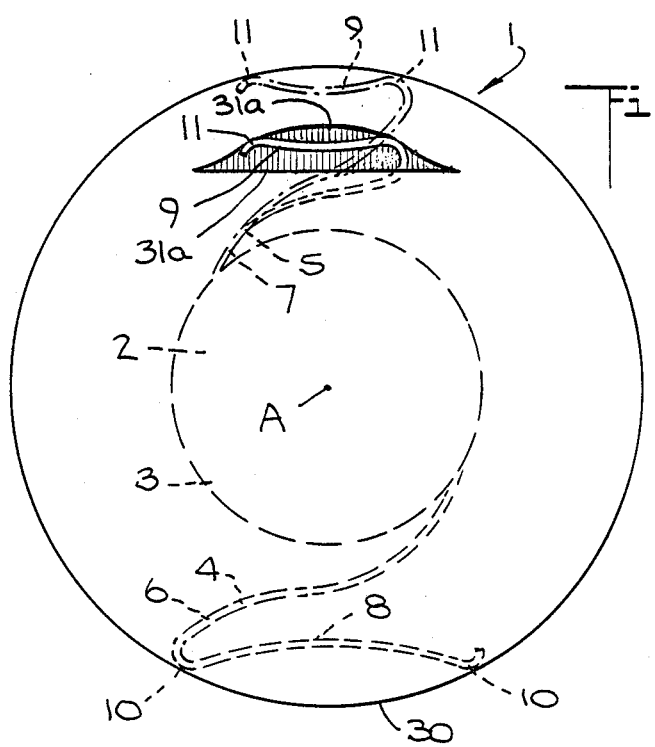
FIG. 5 is a view similar to FIG. 4, showing the intraocular lens trailing haptic just passing interiorly of the parted lips of the incision, and further illustrating by solid dotted line the final internal disposition of such lens as completely inserted and implanted, and still further illustrating by hollow dotted line, for comparison, the corresponding final disposition of the FIG. 1 PRIOR ART intraocular lens.

However, once this has been accomplished, as shown in FIG. 5, incision lips 31a, 31a may be conveniently spread apart a few millimeters in the central region of the incision, preferably by the surgeon pulling the center of the upper lip in a direction away from the lower lip by a distance of a few millimeters, to form a substantially central gap, even though this distorts incision 31 and results in the drawing of its ends slightly towards each other so as to decrease the composite incision length, since the remaining exposed trailing haptic 5 is only about 2-3 mm in length, and thus able to negotiate with facility the now shortened composite incision length.

More important, the produced incision gap provides ample room for the surgeon to manipulate trailing haptic 5 to pass the same through the "gaped" central portion of incision 31 without the need for cumbersome pushing and distortion of trailing stem 7 and more critically of trailing limb 9 and its outwardly projecting pair of lobes 11,11 through incision 31, and especially without the need for intense squeezing of lens 1 to deflect the same inwardly in a direction towards the tissue points in angle groove 30 with which the leading lobes 10,10 are already in seating engagement, in an attempt to enable trailing limb 9 and its lobes 11,11 to clear incision 31 and reach a level inwardly thereof sufficiently to approach and engage its lobes 11,11 with an adjacent tissue portion in angle groove 30 generally diametrically opposite that engaged by leading lobes 10,10.

Instead, as is clear from a comparison of FIGS. 4 and 5, by reason of the shorter 2-3 mm length of trailing limb 9, trailing haptic 5 may be simply gently pressed in inward direction by exerting minimum pressure just sufficient to deflect lens 1 inwardly of the centrally located gap, while the gap is so maintained, and at the same time while manipulating trailing limb 9, e.g. by slight tilting, to clear the gap and more readily approach and engage its lobes 11,11 with the pertinent adjacent tissue portion in angle groove 30, for desired positioning of lens 1 in spaced relation to natural lens 26.

The stated 2-3 mm length of trailing limb 9 is relatively critical, since it determines the corresponding center to center spacing of the trailing contact lobes 11,11, i.e. the length from the crest of one such lobe to the crest of the other (cf. FIG. 2).

Although this center to center, or crest to crest, length between lobes 11,11 is actually slightly less than the length between the transverse end edges of limb 9, as earlier noted, the slight difference therebetween may be regarded as negligible in that lobes 11,11 have a very small radius of curvature, e.g. about 0.125-0.25 mm, such that for a length of limb 9 of about 2-3 mm, a center to center, or crest to crest, spacing of contact lobes 11,11 of about 1-2.5 mm will be provided.

For all practical purposes, therefore, the length of limb 9 and the center to center, or crest to crest, spacing between lobes 11,11 may both be regarded as essentially the same, i.e. effectively about 2-3 mm, as compared to the usual 5.75-5.85 mm center to center, or crest to crest, distance of the lobes of the conventional 6 mm length transverse edge portion-containing haptic having such lobe radius of 0.125-0.25 mm.

In this context, a trailing haptic transverse edge portion or limb having an end to end length substantially shorter than about 2 mm would eliminate the advantage of separated two-point contact of the trailing lobes thereon with adjacent tissue points of the eye and instead result in unduly short line contact tantamount to a single gross point contact of poor fixation stability. On the other hand, a trailing haptic transverse edge portion or limb having an end to end length substantially longer than about 3 mm would not allow the surgeon to take full advantage of the "gaping" of incision 31, but rather would resurrect the original problem and result in the need for intense squeezing and distortion of the intraocular lens, and consequent high risk of injury to the intact natural lens.

The foregoing insertion procedure is thus able to be carried out under minimum deflection of lens 1, due to the resiliently deflectable nature of haptics 4 and 5, and minimum risk of disturbance or dislodging of the previously positioned leading lobes 10,10 relative to their adjacent tissue portion in angle groove 30, or of twisting optic 2 out of its generally continuously maintained parallel relation to natural lens 26, and in turn under maximum inhalation of contact with natural lens 26 by any part of lens 1 during the implantation.

As shown in FIG. 5, once lens 1 is inserted, trailing haptic 5 will assume the position relative to angle groove 30 as depicted in solid dotted line. This is to be compared with the analogous position assumed by trailing haptic 5' of the PRIOR ART lens 1' of FIG. 1, as alternatively depicted in FIG. 5 by hollow dotted line.

Although the finite dimensions involved are relatively small, it will be appreciated from FIG. 5 that because of the shorter effective length of about 2–3 mm of trailing limb 9, relative to the longer or standard 6 mm length of leading limb 8, as well as of both limbs 8' and 9' of the PRIOR ART lens 1' of FIG. 1, trailing lobes 11,11 must extend radially outwardly a slight distance beyond the level of trailing lobes 11',11' of the known lens construction of FIG. 1, in order to seat more fully against the adjacent tissue portion in angle groove 30, given that both haptics are desirably deflected radially inwardly to the same degree.

This is because the corresponding chord represented by the shorter length of trailing limb or transverse edge portion 9 is in turn smaller than the chord represented by the longer or standard length of leading limb or transverse edge portion 9' of the known lens construction of FIG. 1.

For instance, at an overall longitudinal distance D of about 13 mm for lens 1 in relaxed or undeflected haptic condition, and a diameter of about 6 mm for optic 2, the radial distance between optic axis A and leading lobes 10,10 may be about 6.3 mm, while that between optical axis A and trailing lobes 11,11 may be about 6.7 mm, thereby providing an approximately 0.4 mm differential between these radial distances.

To compensate for this approximately 0.4 mm differential, the dimension of trailing haptic 5 in generally radial direction outwardly to trailing lobes 11,11 may be made slightly larger than the corresponding dimension of leading haptic 4 in generally radial direction outwardly to leading lobes 10,10, i.e. as measured from the center or optical axis A of optic 2 to the corresponding pair of lobes. This may be accomplished by differential sizing of the two haptics, or simply by providing lobes 11,11 slightly more pronounced or acute in outwardly projecting crest configuration than lobes 10,10, or by similar expedient.

The optic may be made of polymethylmethacrylate (PMMA) or other suitable material. The haptics may be made of shape retaining, limitedly resilient, deflectable material, such as a suitable plastic, e.g. polymethylmethacrylate (PMMA).

Of course, the optic will be formed of suitable light focusing material having the desired optical characteristics, and all materials used for the corrective lens must be compatible with the internal environment of the eye, and thus nontoxic. After implantation, the intraocular lens will advantageously retain its desired optical and other characteristics.

It will be appreciated that the foregoing specification and accompanying drawings are set forth by way of illustration and not limitation of the present invention, and that various modifications and changes may be made therein without departing from the spirit and scope of the present invention which is to be limited solely by the scope of the appended claims.

What is claimed is:

1. Corrective intraocular lens for use as an anterior chamber lens with an intact natural eye lens for correcting high myopia thereof, by insertion through an incision into the eye and implantation in the anterior chamber in spaced relation to the natural lens, which comprises a lens body, and a pair of generally diametrically opposed resiliently deflectable position fixation haptics extending outwardly from the lens body and arranged for positioning the intraocular lens in the eye in spaced relation to the natural lens, the haptics constituting a leading haptic and a trailing haptic, each comprising a pliable strand having a stem portion attached to the lens body and a limb portion extending from the stem portion and terminating in a transverse edge portion disposed crosswise of a longitudinal diametric line passing through the lens body and intersecting both transverse edge portions, each transverse edge portions having a pair of laterally spaced apart and outwardly projecting contact lobes at the corresponding transverse ends thereof for engaging an adjacent eye tissue portion at a corresponding pair of spaced apart tissue points, whereby to form two generally diametrically opposed pairs of laterally spaced apart fixation points for positioning the intraocular lens in the eye, the trailing haptic transverse edge portion having a length of about 2–3 mm, the lens body having a diameter of at least about two times the length of the trailing haptic transverse edge portion, and the leading haptic transverse edge portion having a length substantially larger than about 2–3 mm, inserted into the eye through an incision of length corresponding substantially to the lens body diameter, by first snaking the leading haptic through the incision, next passing the lens body through the incision and positioning the leading haptic contact lobes in engagement with a said eye tissue portion distal from the incision, and then passing the trailing haptic through the incision by maintaining the lips of the incision slightly spaced apart to form an enlarged gap between the lips in which the widest part of the gap is located centrally of the incision, and moving the trailing haptic through the widest part of the gap, while exerting minimum pressure on the intraocular lens in a direction towards the previously positioned leading haptic contact lobes just sufficient to deflect the trailing haptic inwardly of the gap, and while manipulating the trailing haptic transverse edge portion to clear the gap and approach and engage its contact lobes with a corresponding said eye tissue portion proximate to the incision, for positioning the intraocular lens in spaced relation to the natural lens, with minimum risk of contact with the natural lens by the intraocular lens during the implantation.

2. Lens of claim 1 wherein the lens body diameter is about 6 mm, and the leading haptic transverse edge portion length is about 6 mm.

3. Lens of claim 2 wherein the longitudinal dimension in generally diametric direction between the opposed pairs of leading haptic lobes and trailing haptic lobes is about 13 mm.

4. Lens of claim 1 wherein each haptic is formed as a generally sinusoidal continuous strand having its stem portion attached to the lens body in the vicinity of the lens body periphery.

5. Lens of claim 1 wherein the dimension of the trailing haptic in generally radial direction between the optical axis of the lens body and the trailing haptic lobes is slightly larger than the corresponding dimension of the leading haptic in generally radial direction between the optical axis of the lens body and the leading haptic lobes, sufficient to compensate for the larger length of the leading haptic transverse edge portion relative to the trailing haptic transverse edge portion length, for more precise positioning of the intraocular lens with the contact lobes of the haptics in engagement with the respective adjacent eye tissue portions.

6. Method of implanting the lens of claim 1 in the anterior chamber of an eye for correcting high myopia of the natural eye lens, comprising inserting the intraocular lens into the anterior chamber of an eye, having an intact natural eye lens, through an incision of length corresponding substantially to the lens body diameter, and located sightly anteriorly spaced from the scleral spur and slightly closer than the scleral spur to the optical axis of the eye, for positioning the generally diametrically opposed leading and trailing transverse edge portions of the haptics in the anterior angle groove, at corresponding generally diametrically opposed eye tissue portions of such groove, by first snaking the leading haptic through the incision, next passing the lens body through the incision and positioning the leading haptic contact lobes in engagement with a said eye tissue portion distal from the incision, and then passing the trailing haptic through the incision by maintaining the lips of the incision slightly spaced apart to form an enlarged gap between the lips in which the widest part of the gap is located centrally of the incision, and moving the trailing haptic through the widest part of the gap, while exerting minimum pressure on the intraocular lens in a direction towards the previously positioned leading haptic contact lobes just sufficient to deflect the trailing haptic inwardly of the gap, and while manipulating the trailing haptic transverse edge portion to clear the gap and approach and engage its contact lobes with a corresponding said eye tissue portion proximate to the incision, for positioning the intraocular lens in spaced relation to the natural lens, with minimum risk of contact with the natural lens by the intraocular lens during the implantation.

7. Method of claim 6 wherein the lens body diameter is about 6 mm, and the leading haptic transverse edge portion length is about 6 mm.

8. Method of claim 7 wherein the longitudinal dimension in generally diametric direction between the opposed pairs of leading haptic lopes and trailing haptic lobes in about 13 mm.

9. Method of claim 6 wherein each haptic is formed as a generally sinusoidal continuous strand having its stem portion attached to the lens body in the vicinity of the lens body periphery.

10. Method of claim 6 wherein the dimension of the trailing haptic in generally radial direction between the optical axis of the lens body and the trailing haptic lobes is slightly larger than the corresponding dimension of the leading haptic in generally radial direction between the optical axis of the lens body and the leading haptic lobes, sufficient to compensate for the larger length of the leading haptic transverse edge portion length, for more precise positioning of the intraocular lens with the contact lobes of the haptics in engagement with the respective adjacent eye tissue portions.

11. Method of claim 6 wherein the incision includes a first lip facing towards the optical axis of the eye and a second lip facing away from such eye axis, and the maintaining of the lips slightly spaced apart includes lifting the central portion of the first lip in a direction outwardly and away from the second lip and from such eye axis and towards the adjacent portion of the scleral spur, by a distance of a few millimeters.

* * * * *